(12) United States Patent
Carson et al.

(10) Patent No.: US 10,194,917 B1
(45) Date of Patent: Feb. 5, 2019

(54) TOURNIQUET WITH LEVER TENSIONING MECHANISM

(71) Applicants: William R. Carson, Summersville, WV (US); William Crossingham Cannon, Concord, NC (US); Daniel Pompei Cedrone, Huntersville, NC (US)

(72) Inventors: William R. Carson, Summersville, WV (US); William Crossingham Cannon, Concord, NC (US); Daniel Pompei Cedrone, Huntersville, NC (US)

( * ) Notice: Subject to any disclaimer, the term of this patent is extended or adjusted under 35 U.S.C. 154(b) by 0 days.

(21) Appl. No.: 15/914,054

(22) Filed: Mar. 7, 2018

(51) Int. Cl.
*A61B 17/132* (2006.01)

(52) U.S. Cl.
CPC ....... *A61B 17/1327* (2013.01); *Y10T 24/2147* (2015.01)

(58) Field of Classification Search
CPC .............. A61B 17/132; A61B 17/1322; A61B 17/1325; A61B 17/1327; Y10T 24/2143; Y10T 24/2147; Y10T 24/2164; Y10T 24/2192
See application file for complete search history.

(56) References Cited

U.S. PATENT DOCUMENTS

| | | | | |
|---|---|---|---|---|
| 160,020 A * | 2/1875 | Kincaid | ................. | A44B 11/04 24/71 ST |
| 268,723 A * | 12/1882 | Parker | ..................... | A44C 5/24 24/71 R |
| 478,120 A * | 7/1892 | Mead | ..................... | A44B 11/04 24/70 SK |
| 721,162 A * | 2/1903 | Denain | .............. | A61B 17/1327 606/203 |
| 1,302,062 A * | 4/1919 | McFarlane | ......... | A61B 17/1327 606/203 |
| 1,447,967 A * | 3/1923 | Davis | ..................... | A44B 11/25 24/163 R |
| 1,771,689 A * | 7/1930 | Owen | ................. | A61B 17/1327 606/203 |
| 1,870,052 A * | 8/1932 | Jones | ................. | A61B 17/1327 606/203 |
| 1,962,285 A * | 6/1934 | Robinson | ........... | A61B 17/1327 24/191 |
| 2,017,948 A * | 10/1935 | Chenery | ............ | A61B 17/1327 606/203 |
| 2,156,870 A * | 5/1939 | Rineer | ............... | A61B 17/1327 24/196 |
| 2,576,986 A * | 12/1951 | Windsor | ................ | B65D 63/16 24/134 R |
| 2,825,109 A * | 3/1958 | Nelson | ................. | A44B 11/125 24/273 |

(Continued)

*Primary Examiner* — Ryan J Severson
(74) *Attorney, Agent, or Firm* — Trego, Hines & Ladenheim, PLLC

(57) ABSTRACT

A tourniquet includes: a baseplate with first and second ends; a strap having first and second ends, the strap having a first portion adjacent its first end, and a second portion adjacent its second end; a lever with proximate and distal ends, wherein the proximate end is pivotally connected to the baseplate, and the distal end is free; wherein the first end of the strap is pivotally connected to the lever intermediate to the proximal and distal ends; and a connector assembly operable to selectively connect the second portion of the strap to the baseplate, so as to form a closed loop, the connector assembly operable to permit a length of the closed loop to be adjusted.

27 Claims, 13 Drawing Sheets

(56) References Cited

U.S. PATENT DOCUMENTS

| | | | | |
|---|---|---|---|---|
| 2,893,394 | A * | 7/1959 | Thomsen | A61B 17/1327 24/200 |
| 4,564,981 | A * | 1/1986 | Knox | A44B 11/125 24/193 |
| 4,777,703 | A * | 10/1988 | Knox | A44B 11/125 24/170 |
| 6,884,254 | B2 * | 4/2005 | Brooks | A61B 17/1327 24/71 R |
| 7,842,067 | B2 | 11/2010 | Esposito | |
| 7,947,061 | B1 * | 5/2011 | Reis | A61B 17/1322 606/203 |
| 8,608,036 | B2 * | 12/2013 | Mori | A45F 3/14 224/219 |
| 8,888,807 | B2 | 11/2014 | Esposito | |
| 8,978,944 | B2 * | 3/2015 | Mori | A45F 3/14 224/219 |
| 9,663,255 | B2 * | 5/2017 | Ritola | B65B 13/02 |
| 9,750,507 | B2 * | 9/2017 | Brub | A61B 17/1327 |
| 2003/0028215 | A1 * | 2/2003 | Brooks | A61B 17/1327 606/203 |
| 2005/0049630 | A1 * | 3/2005 | Ambach | A61B 17/1327 606/203 |
| 2012/0215254 | A1 * | 8/2012 | Brub | A61B 17/1327 606/203 |
| 2012/0246895 | A1 * | 10/2012 | Lee | B60P 7/083 24/68 E |
| 2016/0302799 | A1 | 10/2016 | Esposito | |
| 2017/0354422 | A1 * | 12/2017 | Brub | A61B 17/1327 |
| 2018/0042616 | A1 * | 2/2018 | Demas | A61B 17/1327 |

\* cited by examiner

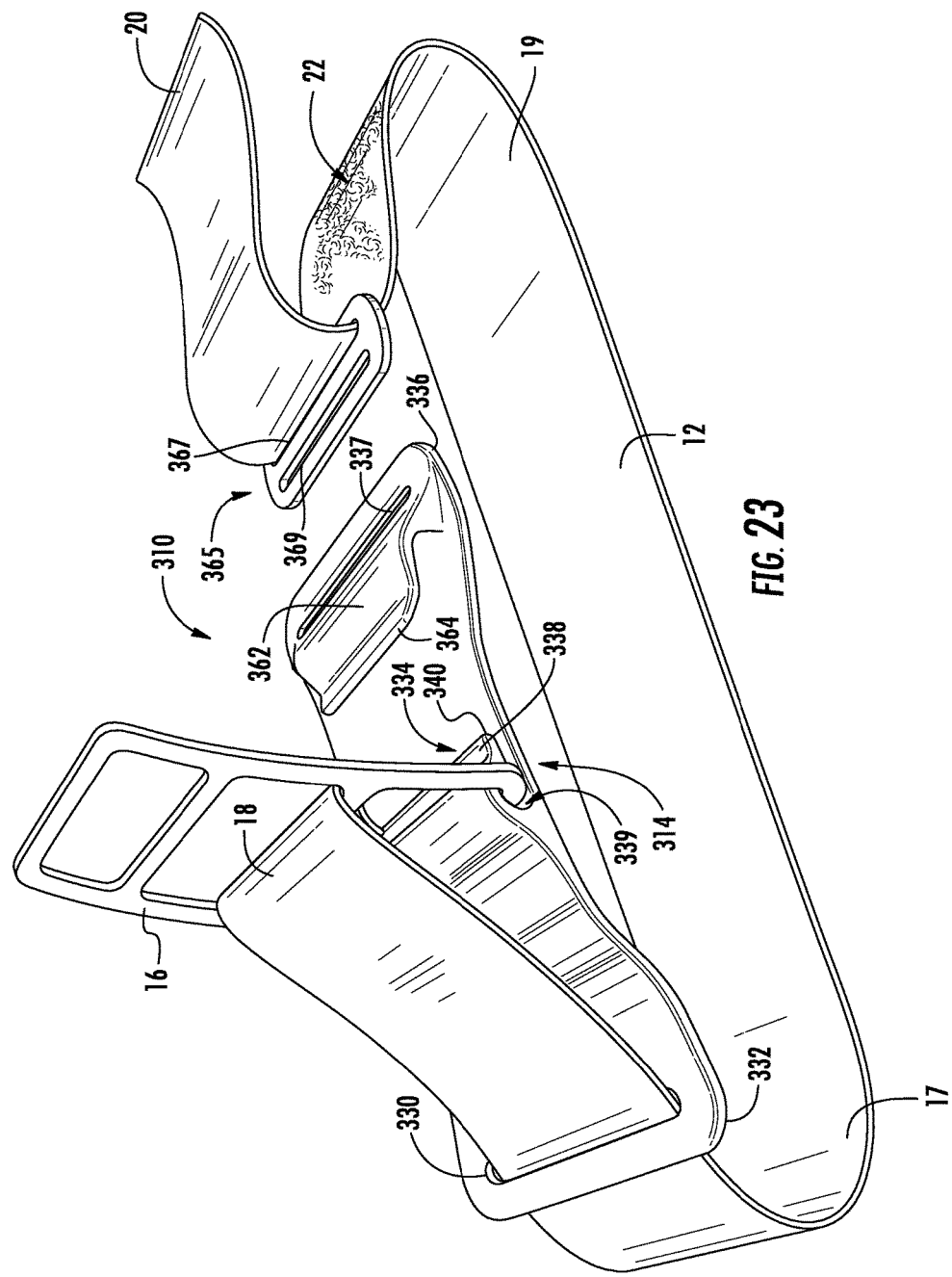

TOURNIQUET WITH LEVER TENSIONING MECHANISM

BACKGROUND OF THE INVENTION

This invention relates generally to tourniquets and more particularly to self-applied tourniquets.

Tourniquets are known and used for stopping blood flow preventing massive hemorrhage which can result in death. Massive hemorrhage remains the number one cause of preventable death on the battlefield despite current tourniquet use. Catastrophic limb injuries are not unique to the battlefield and can occur in the civilian sector with motor vehicle accidents, industrial accidents, agricultural accidents and active shooter episodes.

When a major blood vessel is cut, a short period of time is available to stop the flow of blood and prevent massive hemorrhage and ultimately death.

It is helpful to provide a tourniquet that can be self-applied by the injured person as medical personnel may not be readily available. Self-applied tourniquets are known and used in the art.

One problem with existing self-applied tourniquets is that they require the use of a winding stick, (or windlass), which is used to tension the tourniquet and occlude the arterial blood flow. The stick and other parts of the tourniquet can protrude, catch on objects, become dislodged from its locked position and at times not work. With the windlass dislodged, tourniquet effect is lost creating problems during transport and possibly demise. The windlass also adds weight and increases the bulk of the tourniquet, making it more difficult to store and to carry.

BRIEF SUMMARY OF THE INVENTION

This problem is addressed by a self-applied tourniquet utilizing a lever tensioning mechanism.

According to one aspect of the technology described herein, a tourniquet includes: a baseplate with first and second ends; a strap having first and second ends, the strap having a first portion adjacent its first end, and a second portion adjacent its second end; a lever with proximate and distal ends, wherein the proximate end is pivotally connected to the baseplate, and the distal end is free; wherein the first end of the strap is pivotally connected to the lever intermediate to the proximal and distal ends; and a connector assembly operable to selectively connect the second portion of the strap to the baseplate, so as to form a closed loop, the connector assembly operable to permit a length of the closed loop to be adjusted.

According to another aspect of the technology described herein, a tourniquet includes: a baseplate with first and second ends, and a strap guide disposed at the first end; a strap having first and second ends, the strap having a first portion adjacent its first end, and a second portion adjacent its second end, wherein the first portion of the strap is engaged with the strap guide; a lever with proximate and distal ends, wherein the proximate end is pivotally connected to the baseplate, and the distal end is free; wherein the first end of the strap is pivotally connected to the lever intermediate to the proximal and distal ends, such that the lever is movable between released and tightened positions, wherein a free length of the strap extending beyond the baseplate is shorter in the tightened position than in the released position; a locking mechanism operable to secure the lever in the tightened position; and a connector assembly operable to selectively connect the second portion of the strap to the baseplate, so as to form a closed loop, the connector assembly operable to permit a length of the closed loop to be adjusted.

BRIEF DESCRIPTION OF THE DRAWINGS

The invention may be best understood by reference to the following description taken in conjunction with the accompanying drawing figures, in which:

FIG. 23 is a perspective view showing a tourniquet constructed using an alternative baseplate.

DETAILED DESCRIPTION OF THE INVENTION

Figure 1:
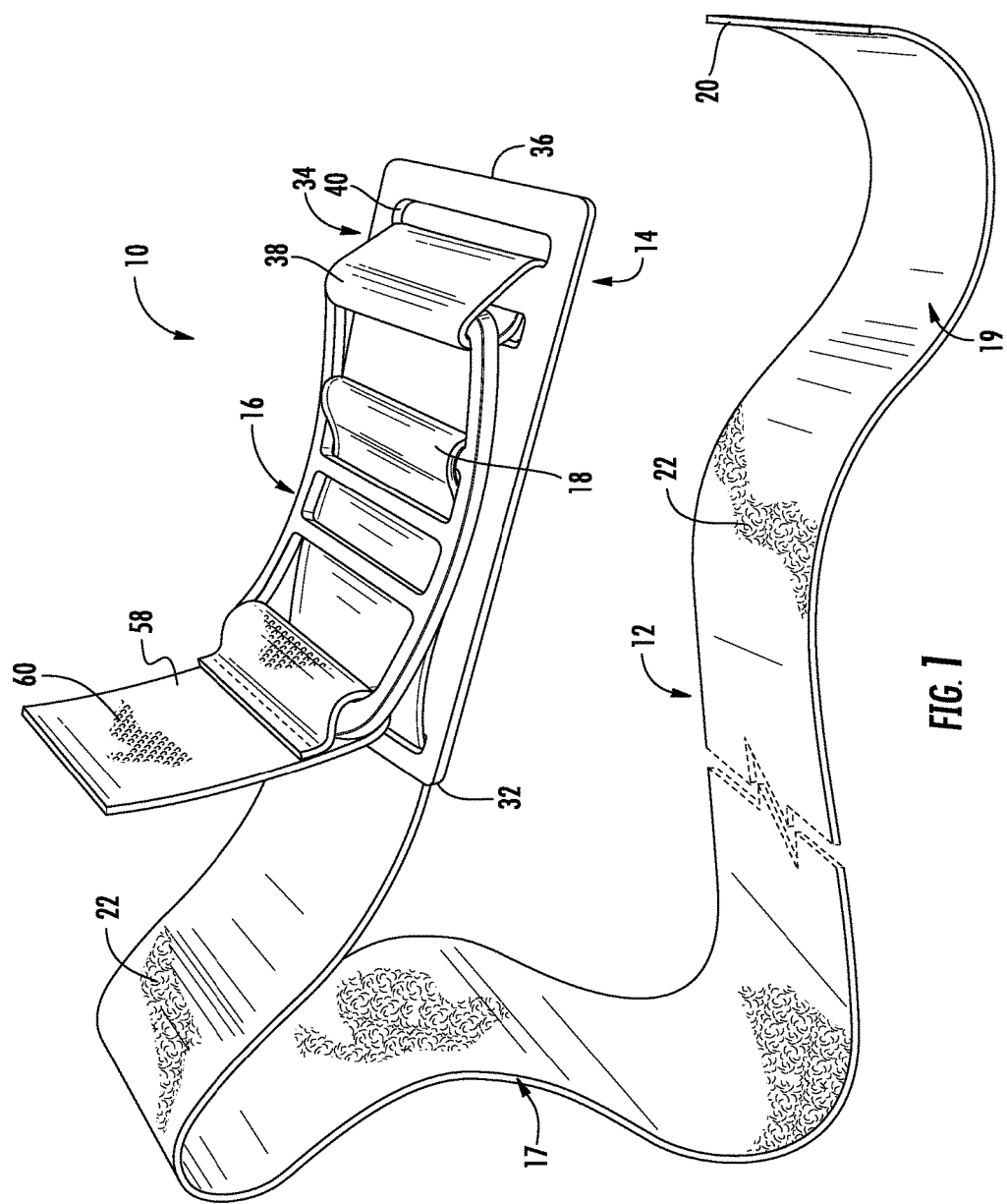
FIG. 1 is a schematic perspective view showing an exemplary tourniquet.
Figure 2:
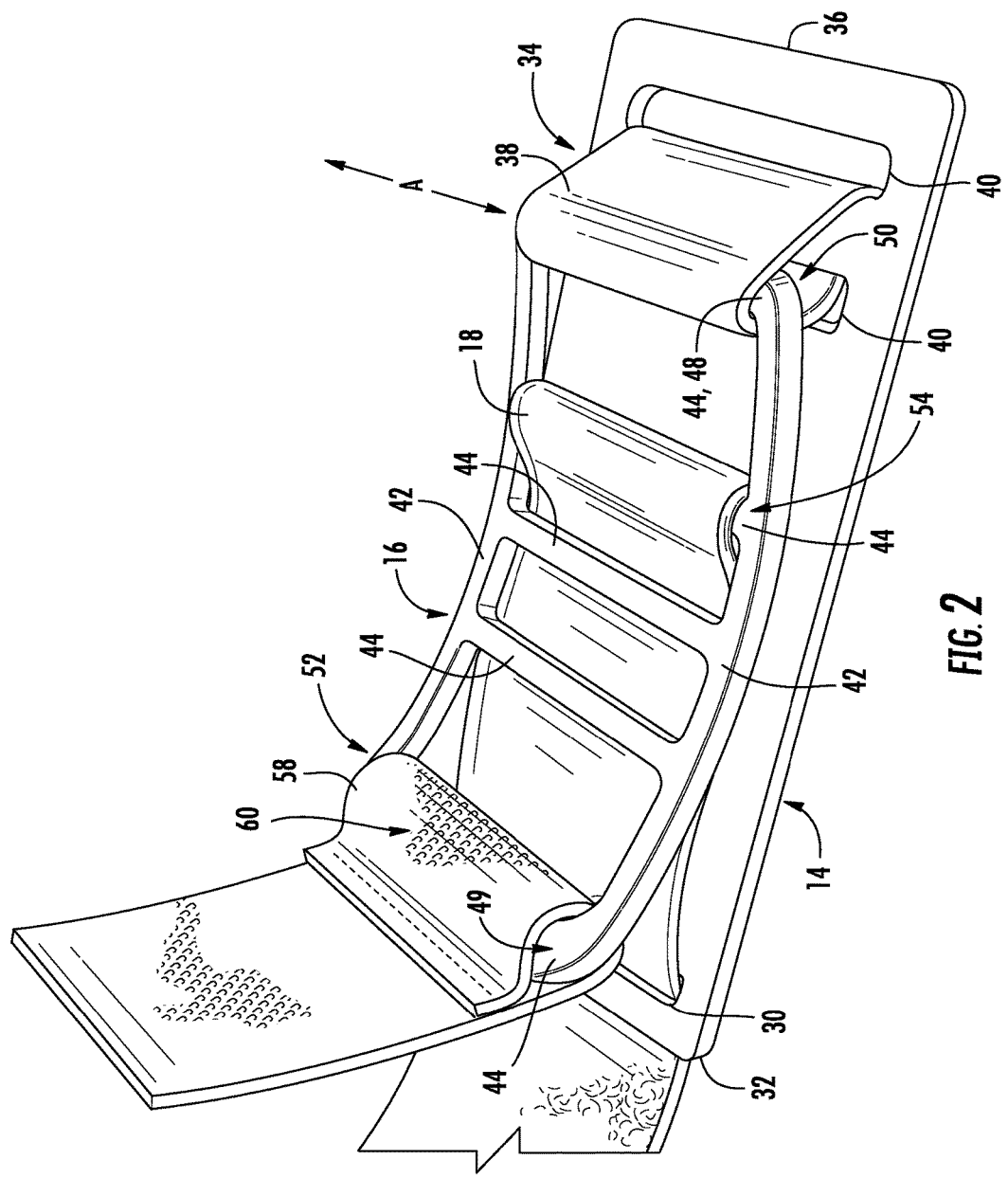
FIG. 2 is an enlarged view of a portion of FIG. 1.

Referring to the drawings wherein identical reference numerals denote the same elements throughout the various views, FIGS. 1 and 2 illustrate an exemplary tourniquet 10. The basic components of the tourniquet 10 are a strap 12, a baseplate 14, and a lever 16, each of which will be described in more detail below.

The strap 12 is an elongated flexible member extending continuously between first and second ends 18, 20 respectively. For purposes of reference the strap may be described as having a first portion 17 adjacent the first end 18 and a second portion 19 adjacent the second end 20. The strap 12 may be constructed from any material which is flexible and which is capable of withstanding a predetermined tensile force sufficient to cut off (occlude) blood flow in a patient's limb. Nonlimiting examples of suitable materials for the strap 12 include fabric and other textiles, plastics, metals, and combinations thereof. The strap 12 may be configured as a flat, band-like material as shown or may have another form, such as a tube, rope, or cable. In the illustrated example, the strap 12 comprises woven nylon webbing.

The strap 12 incorporates suitable releasable connectors 22. As used herein the term "releasable" refers to a connection that can be coupled and uncoupled in ordinary use without damage to the connectors. In some aspects, the connection is releasable without resorting to the use of tools. By way of example and not of limitation, examples of releasable connectors include buttons, snaps, stud-type snap fasteners, magnets, or hook-and-loop type fasteners (e.g., VELCRO). In the illustrated example, the strap 12 incorporates hook-and-loop type fasteners. These connectors are configured such that the strap 12 may be coiled into a compact bundle and secured to itself. These connectors are further configured such that the second portion 19 of the strap 12 may be folded over and attached to itself. For example, one face or side of the strap 12 may incorporate a loop portion of a hook-and-loop fastener over all or a part of its area, and the opposed face or side of the strap 12 may incorporate a combined hook and loop portion of a hook-and-loop fastener over all or a portion of its area.

Figure 3:
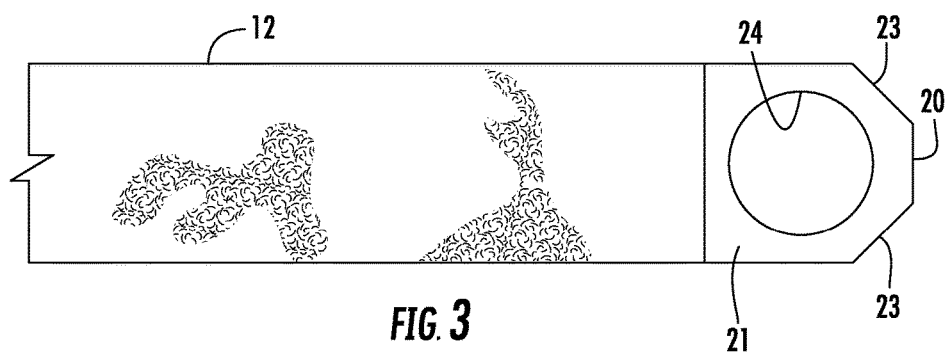
FIG. 3 is a schematic top plan view of a portion of an alternative strap having a finger hole formed therein.

FIG. 3 illustrates examples of optional features which may be provided to make it easier to manipulate the second end 20 of the strap 12. In one example, an area at the second end 20 of the strap 12 includes an end marking 21 such as words, letters, symbols, patterns or colors which serve to make the second end 20 easily identifiable. In another example, the second end 20 may be provided with chamfered corners 23 to provide a lead-in element for feeding the second end 20 through the slots described below. In another example, the terminal part of the second end 20, for example about 19 mm (¾ in.) may be smooth and free of fasteners or other protrusions to facilitate easy grasping. A finger hole 24 may be provided at or near the second end 20. The finger hole 24 may be sized to permit use while wearing gloves.

Figure 4:
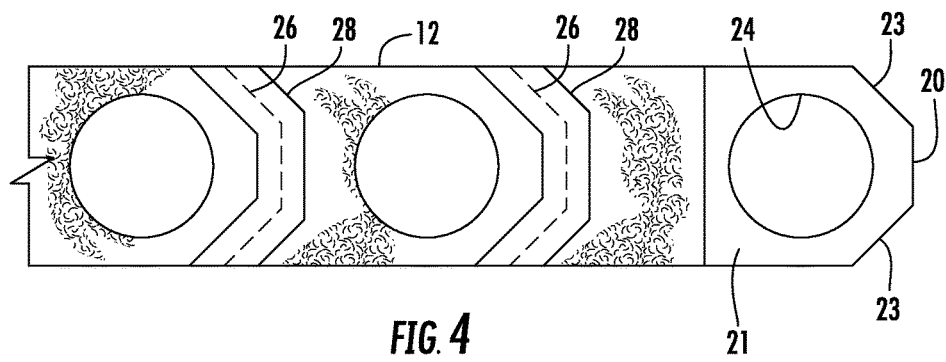
FIG. 4 is a schematic top plan view of a portion of an alternative strap incorporating cut markings.

The basic length of the strap 12 may be selected to permit use with a range of users and for different limbs. For example, the basic length may be suitable to encircle the largest limb of the largest possible user. A user may choose to shorten the strap 12 to avoid excess length and to reduce weight, permitting easier storage and transport. Some means may be provided to make it easier to shorten the strap 12. For example, cut markings 26 indicating predetermined length intervals and/or flat sections 28 configured to facilitate easy cutting with hand tools (e.g., scissors, pocket knife) may be provided along the length of the strap 12, as seen in FIG. 4. The fibers within the flat sections 28 may be consolidated (e.g. by thermal or ultrasonic bonding, adhesive sealing) so as to be resistant to fraying and unraveling after cutting; however, these sections otherwise retain the full strength characteristics of the remainder of the strap 12. Optionally, the cut markings 26 could indicate specific lengths, for example the maximum possible length required for use with a leg, or the maximum possible length required for use with an arm. Portions of the strap 12 near the flat sections 28 and/or cut markings 26 may be configured so that, after cutting, the remaining portion provides one or more of the original distal end features, such as: an end marking, chamfered corners, a smooth, protrusion-free end, or a finger hole.

The baseplate 14 is a relatively thin, plate-like rigid or semi-rigid member. Nonlimiting examples of suitable material for the baseplate 14 include plastics, wood, metals, and combinations thereof. In the illustrated example, the baseplate 14 is constructed as a flat plate of polymeric material with a generally rectangular plan view shape.

Referring to FIG. 2, the baseplate 14 includes a strap guide 30 at a first end 32 thereof (also referred to herein as an aft end). The purpose of the strap guide 30 is to permit axial movement of the strap 12 relative to the baseplate 14, while preventing lateral movement of the strap 12 relative to the baseplate 14. In the illustrated example, the strap guide 30 comprises a slot formed near the first end 32 of the baseplate 14 through which the first end 18 of the strap 12 is threaded. Other guide structures such as rails or flanges (not shown) could be used as an alternative.

The baseplate 14 includes a lever anchor 34. In the illustrated example, the lever anchor 34 comprises a closed loop 38 of nylon webbing or other flexible material which is fed through the lever 16, and a pair of closely-spaced slots 40 formed in the baseplate 14. In the illustrated example the lever anchor 34 is positioned at or near a second end 36 of the baseplate 14, opposite to the first end 32, but other locations are possible.

The lever 16 is a substantially rigid member which is stiff enough to act as a lever. Nonlimiting examples of suitable material for the lever 16 include metals, plastics, wood, composites, and combinations thereof. In the illustrated example, the lever 16 is constructed as a unitary or monolithic metallic element having a pair of side rails 42 interconnected by crossbars 44. The side rails 42 may be curved such that the lever 16 has an arcuate shape when viewed in side elevation.

The lever 16 includes a first pivot element 48 at a first or proximate end 50 thereof. The first pivot element 48 is connected to the lever anchor 34 such that the lever 16 can pivot relative to the baseplate 14, about a pivot axis "A" passing through the first pivot element 48. It is noted that this axis A is shown merely for reference and that its absolute location may vary depending on the tension in the closed loop 38. In the illustrated example, the first pivot element 48 is defined by one of the crossbars 44 which is captured by the closed loop 38 of the lever anchor 34.

The lever 16 is configured such that it can be manually pivoted about the first pivot element, and may include a handle element 49 for the purpose of providing leverage. In the illustrated example, the handle element 49 is defined by another one of the crossbars 44 located at a second or distal end 52 of the lever 16.

Figure 5:
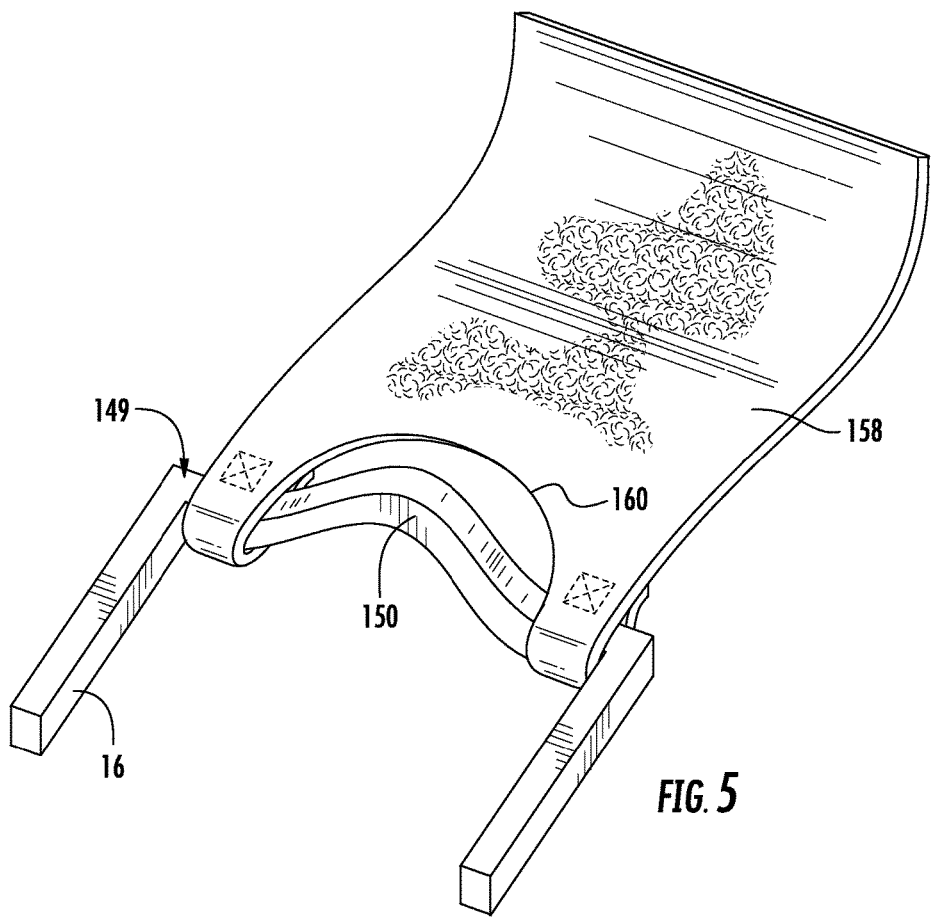
FIG. 5 is a perspective view showing an alternative lever end.

Optionally, the handle element 49 may be contoured or shaped to provide a protruding portion for the purpose of making it easier to grip. For example, FIG. 5 illustrates a variation of a handle element 149 which is curved outwards, defining a convex finger pull 150. This may be implemented in conjunction with a modified lock tab 158 including a cutout 160 to provide access to the finger pull 150.

The lever 16 includes a second pivot element 54 positioned in an intermediate location between the proximate end 50 and the distal end 52. In the illustrated example, the second pivot element 54 is defined by another one of the crossbars 44. The first end 18 of the strap 12 is connected to the second pivot element 54 such that the lever 16 can pivot relative to the strap 12. For example, the first end 18 of the strap 12 may be wrapped around the second pivot element 54 and then secured to itself using conventional stitching.

Figure 6:
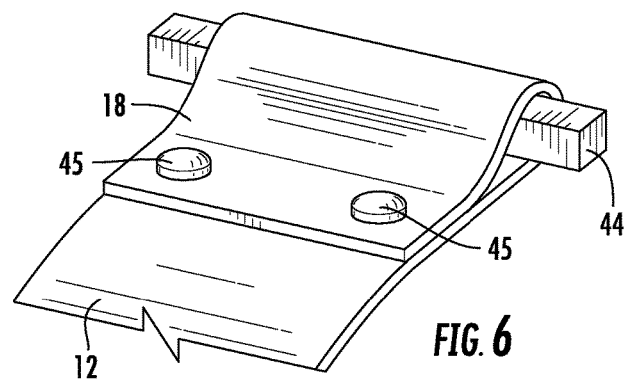
FIG. 6 is a perspective view showing an alternative strap end.

Optionally, the tourniquet 10 may incorporate a means for moving the first end 18 of the strap 12 to different positions between the proximate end 50 and the distal end 52. For example, FIG. 6 shows a first end 18 of the strap 12 wrapped around a representative crossbar 44 and secured to itself using heavy-duty snaps 45 or another similar releasable fastener. The first end 18 could be moved by opening the snaps 45, placing the strap and around a different crossbar, and then re-securing the snaps 45. The effect of moving the first end 18 would be to change the mechanical advantage of the lever 16 on the strap 12, with a corresponding inverse effect on the displacement of the strap 12. This adjustment may be used to tailor the performance of the tourniquet 10 to an individual user's preference.

Collectively, the lever 16, baseplate 14, and strap 12 are assembled such that the lever 16 is movable in a pivoting motion about the pivot axis A. Movement from the released position to the tightened position causes the first end 18 of the strap 12 to be drawn through the strap guide 30. This movement causes a free length of the strap 12, defined as an amount of the strap 12 extending beyond the perimeter of the baseplate 14, to be reduced.

Figure 7:
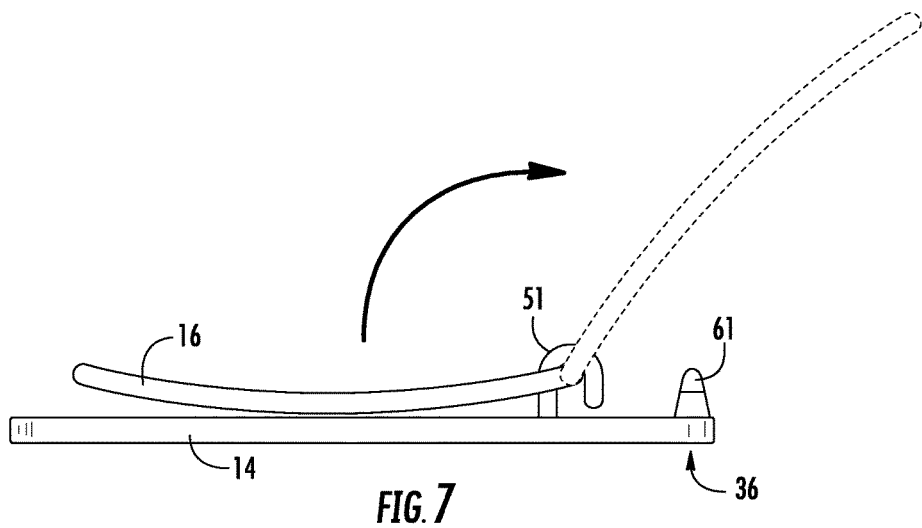
FIG. 7 is a schematic side elevational view showing an alternative embodiment of a baseplate with an integral pivot member.
Figure 8:
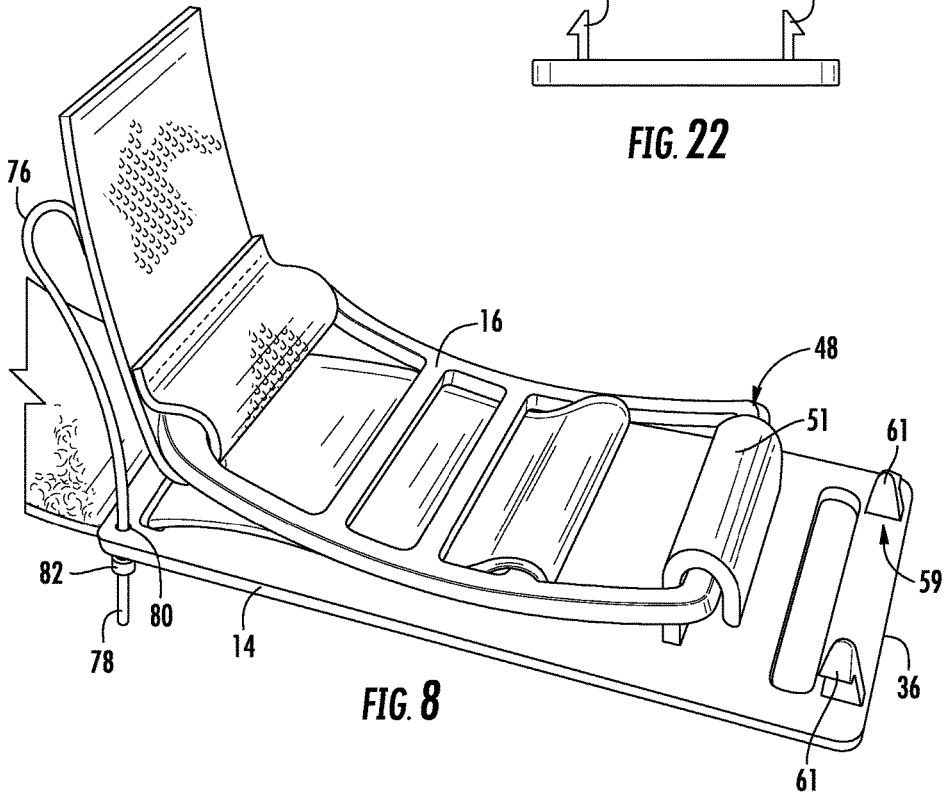
FIG. 8 is a perspective view showing the baseplate and lever of FIG. 7.

Alternative means may be provided for pivotal mounting of the lever 16. For example, FIGS. 7 and 8 illustrate an optional variation of the baseplate 14 in which the closed loop 38 described above is eliminated, and one of the slots 40 is replaced by a rigid, generally U-shaped member 51 which is formed as part of the baseplate 14 and which captures the first pivot element 48 of the lever 16.

Some means are provided for securing the lever 16 in the tightened position. In the example shown in FIG. 1, a lock tab 58 is provided in the form of a strap of flexible material which is looped around the handle element 48 of the lever 16. The lock tab 58 incorporates suitable releasable connectors 60. The illustrated example shows a patch of hook-and-loop fastener material.

Optionally, the lock tab 58 may incorporate one or more features to make it easier to identify and/or manipulate, as described above for the second end 20 of the strap 12, for example, an end marking, chamfered corners, a smooth, protrusion-free end, or a finger hole.

Figure 22:
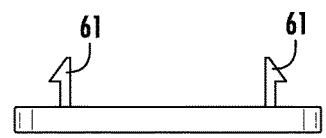
FIG. 22 is a schematic end view of a baseplate showing a latch mechanism.

Alternatively, the lever 16 and/or the baseplate 14 may incorporate a latch or other similar mechanism operable to connect the lever 16 to the baseplate 14, thereby securing the lever in the tightened position. For example, FIGS. 7, 8, and 22 illustrate a latch 59 comprising a pair of spaced-apart generally L-shaped resilient hooks 61 with barbed tips protruding from the baseplate 14 near its second end 36. The hooks 61 are positioned such that the lever 16 can pass around them when it is moved to the tightened position. When the lever 16 reaches the fully tightened position the barbed ends of the hooks 61 engage it and prevent it from being released. If there is a need to release the lever 16, for example if arterial occlusion is not achieved, then the hooks 61 can be released by squeezing them together, or alternatively, the lever 16 could be pulled up with sufficient force to disengage the hooks 61.

The tourniquet 10 includes a "connector assembly" operable to selectively connect the second portion 19 of the strap 12 to the baseplate 14, so as to form a closed loop. The connector assembly is operable to permit a length of the closed loop to be adjusted (i.e., lengthened or shortened). It will be understood that the connector assembly may be a discrete element, or it may be defined in whole or part by the strap 12, the baseplate 14, or some combination thereof.

In the illustrated example, one of the slots 40 described above located at the second end 36 of the baseplate 14 accepts the second end 20 of the strap 12. The second portion 19 of the strap 12 can be passed through the slot 40, pulled to a desired position (i.e., adjusted), and then folded back and connected to the remainder of the strap 12 using the releasable connector 22. This is an example of a "connector assembly".

Figure 9:
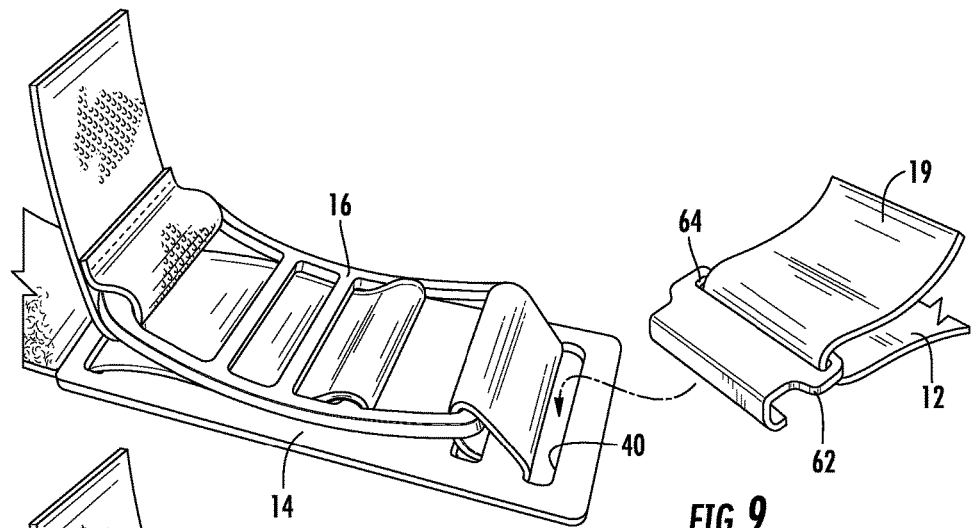
FIG. 9 is a perspective view showing a baseplate and a strap incorporating a hook member.
Figure 10:
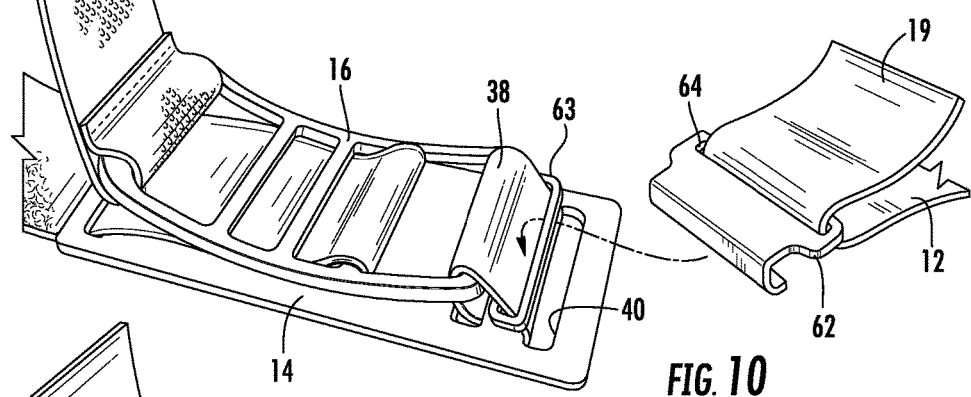
FIG. 10 is a perspective view showing a baseplate and a strap incorporating a hook member.

Alternatively, the second portion 19 of the strap 12 may be connectable to the baseplate 14 using a hook-type connection wherein one of the baseplate 14 and the strap 12 includes a female element, and the other of the baseplate 14 and the strap 12 includes a complementary male element. For example, the second portion 19 of the strap 12 may have a flat hook 62 attached thereto as seen in FIG. 9, with a slot 64 that permits adjustment of the strap 12. The end of the flat hook 62 can in turn be engaged with one of the slots 40 of the baseplate 14. This is another example of a "connector assembly". Alternatively, a different anchor may be provided for the end of the flat hook 62. For example, FIG. 10 shows a variation in which a ring 63 with a generally rectangular shape and made of a rigid material such as metal or plastic is attached to the closed loop 38 of the lever anchor 34. In the illustrated example, the closed loop 38 is simply passed through the center of the ring 63. Alternatively, the ring 63 could be secured to the closed loop 38 using stitching or some other fastening method (not shown) to force it to remain in a specific position. In use, the end of the flat hook 62 can be engaged with the ring 63. This provides a secure connection point and prevents stresses on the baseplate 14, especially the slot 40.

Figure 11:
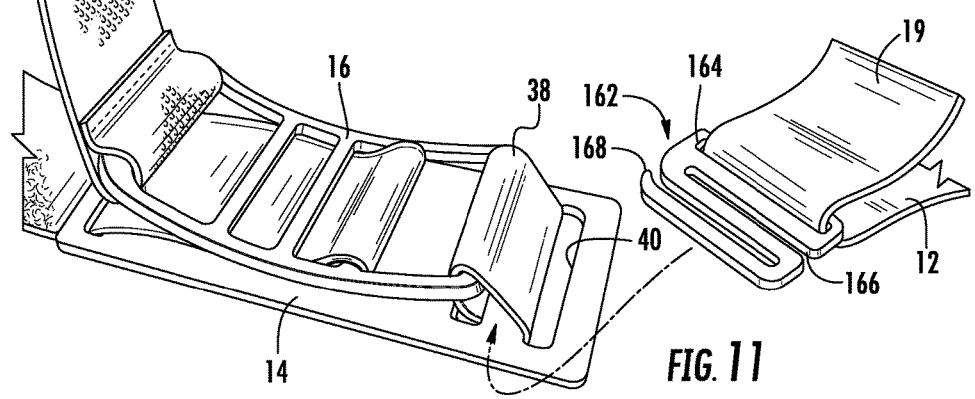
FIG. 11 is a perspective view showing a baseplate and a strap incorporating an alternative hook member.

FIG. 11 shows an example of another type of hook 162 that may be attached to the second portion 19 of the strap 12. The hook 162 includes a slot 164 that permits adjustment of the strap 12. The hook 162 has a generally S-shaped body that defines two separate, parallel engagement slots 166, 168 that are open at opposite sides of the hook body. Either of the engagement slots 166, 168 can be engaged directly with the closed loop 38. This avoids fatigue on the baseplate 14, and permits use from either direction (left or right). This is another example of a "connector assembly".

Figure 12:
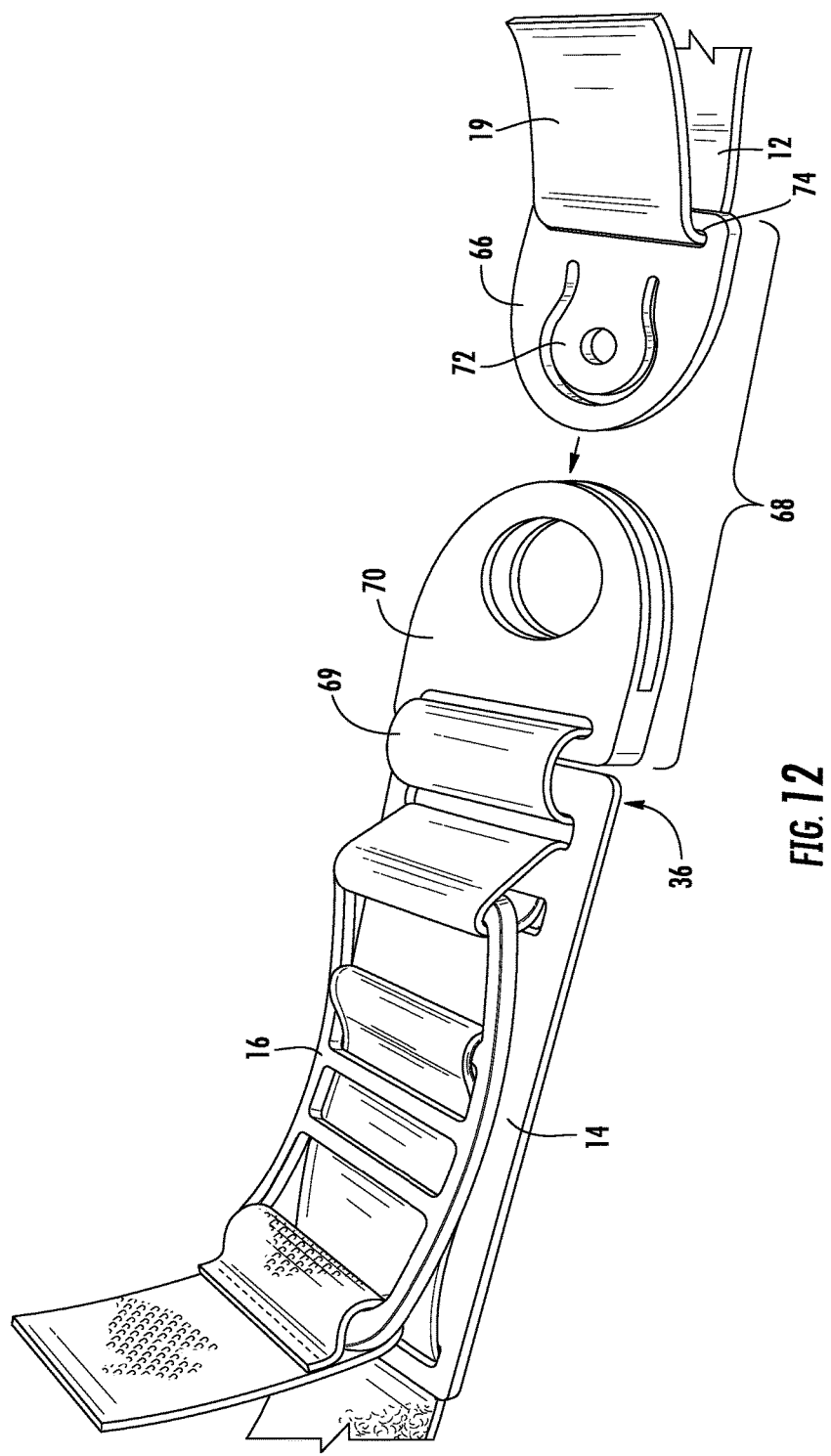
FIG. 12 is a perspective view showing a baseplate and a strap incorporating a snap buckle.

Alternatively, as seen in FIG. 12, the second portion 19 of the strap 12 may have a first half 66 of a known type of connector such as a snap buckle 68 attached thereto, and the second half 70 of the snap buckle 68 may be attached to the second end 36 of the baseplate 14. The two halves of the snap buckle 68 may be engaged by pushing them together, and may be separated by depressing the tang 72 of the first half 70. The first half 70 includes a slot 74 that permits adjustment of the strap 12. This is yet another example of a "connector assembly". The snap buckle 68 (or any of the connector assemblies described above) may be attached directly to the baseplate 14, or by using an intervening strap 69.

Optionally, the tourniquet 10 may incorporate a counter-pull handle, defined as an element which permits a user to grasp and pull the first end 32 of the baseplate 14. In the example shown in FIG. 8, a counter-pull handle 76 comprises a loop of cord with distal ends 78 fed through holes 80 in the baseplate 14 and secured by ferrules 82.

The use of the tourniquet 10 will now be described with reference to FIGS. 13-18. In these figures, the tourniquet 10 is being shown applied to a limb "L" which happens to be a user's thigh; however, it will be understood that the usage steps are similar for any limb.

It is noted that the tourniquet 10 may be stored in a compact configuration by coiling the strap 12 around the baseplate 14 and using the releasable connector 22 of the strap 12 to secure the strap 12 in the coiled configuration. Before carrying out the following steps, the tourniquet 10 would be retrieved and the strap uncoiled to prepare it for use. Alternatively, the tourniquet 10 may be used as a belt by wrapping the strap 12 around a user's torso and using the releasable connector 22 of the strap 12 to secure the strap 12.

Figure 13:
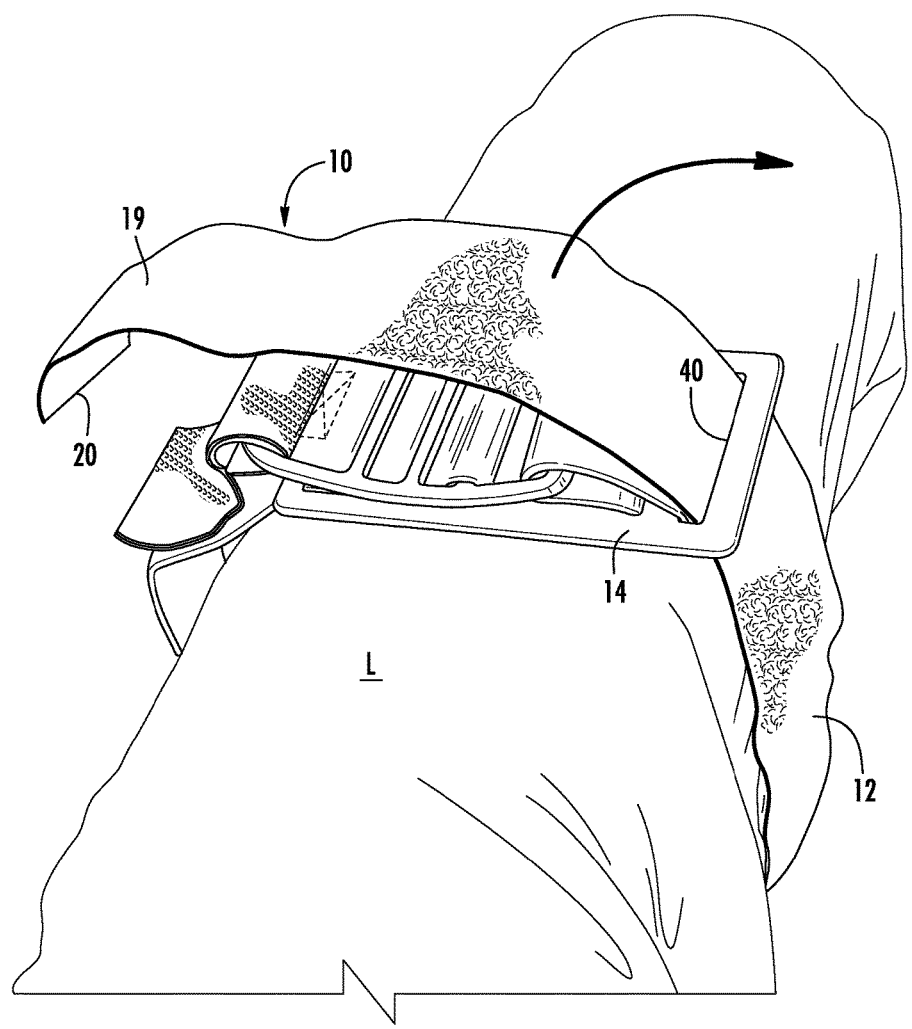
FIG. 13 is a perspective view showing a first step in using the tourniquet of FIG. 1, with the tourniquet being initially applied to the limb of a patient.

Referring to FIG. 13, use begins by placing the tourniquet 10 with the baseplate 14 against the limb L. If the end of the limb L is free, the second portion 19 of the strap 12 may be pre-looped through the slot 40 in the baseplate 14, or the flat hook 62 or snap buckle 68 described above may be pre-connected. Then the entire tourniquet 10 already formed in a closed loop may be slipped over the free end of the limb L and moved into position. However, there may be circumstances where this is undesirable or impossible. For example, a user's foot may be trapped underneath a vehicle or building rubble. Under such circumstances, the second portion 19 of the strap 12 would initially be disconnected from the baseplate 14. After bringing the second portion 19 around the limb L, the second portion 19 of the strap 12 would then be connected to the baseplate 14, i.e., by using the slot 40, the flat hook 62, or the snap buckle 68 as provided.

Figure 14:
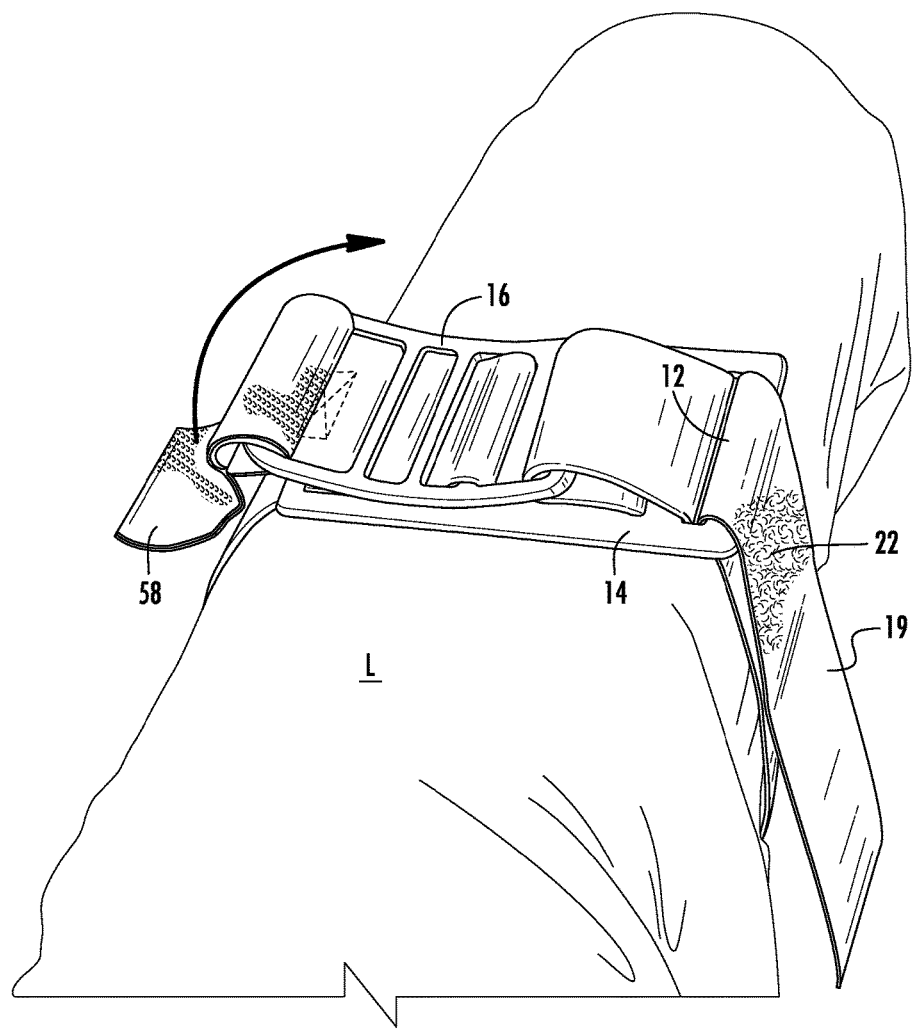
FIG. 14 is a perspective view showing a second step in using the tourniquet of FIG. 1, with the strap being secured in a closed loop around the limb.

In a second step, shown in FIG. 14, the second portion 19 of the strap 12 is wrapped around the body of the strap 12 and is pulled taut in order to remove the majority of the slack from the strap 12. The term "majority of the slack" refers to pulling the strap 12 sufficiently taut so that operation of the lever 16 will tighten the strap 12 enough to cut off blood flow to the limb L. The exact tension to be used will depend on the specific user. The user may be trained or provided with instructions as to how to properly remove the majority of the slack. The step of removing the majority of the slack may also be referred to as pre-tensioning the tourniquet 10. If the optional counter-pull handle 76 is used, the user may pull this in opposition to the pulling taut motion, either to make this step easier or to prevent unwanted movement of the tourniquet 10 relative to the limb L. The lever itself 16 could alternatively be used for this purpose.

Once the slack is pulled out, the strap 12 is connected to itself in order to form (collectively with the baseplate 14) a closed loop around the limb L. The connection may be accomplished using the releasable fasteners 22.

Figure 15:
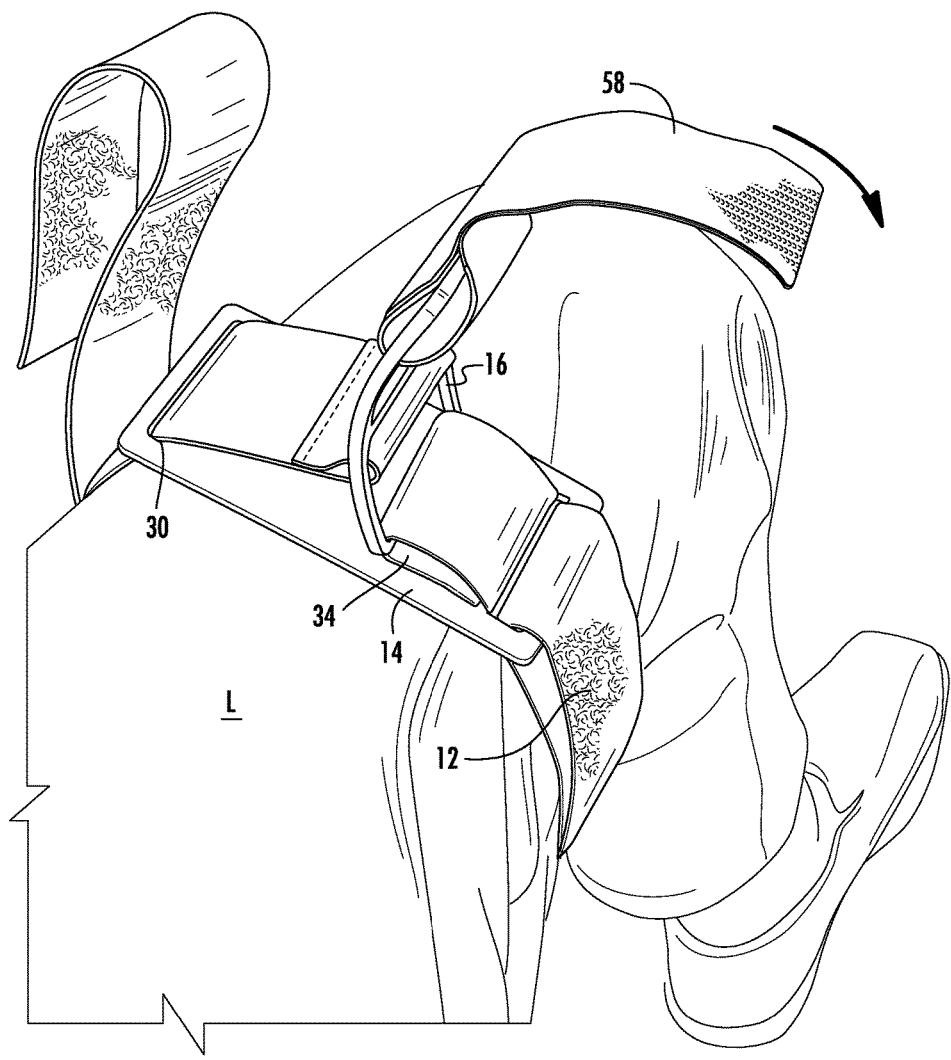
FIG. 15 is a perspective view showing a third step in using the tourniquet of FIG. 1, with a lever thereof being moved towards a tightened position.

In a third step, shown in FIG. 15, the lever 16 is pivotally actuated by moving it from the released position towards the tightened position, as shown by the arrow in the figure. This may be done, for example by pulling sharply on the lock tab 58 or the lever 16, itself, in a continuous motion. As the lever 16 is pivotally actuated, the first end 18 of the strap 12 is drawn through the strap guide 30, while simultaneously the lever 16 applies tension to the lever anchor 34. The overall effect is to shorten the length of the closed loop formed by the baseplate 14, the lever 16, and the strap 12, thus supplying clamping pressure to the limb L and cutting off blood flow in the blood vessel. The strap guide 30 helps prevent the strap 12 from becoming twisted or misaligned during the tightening operation.

Figure 16:
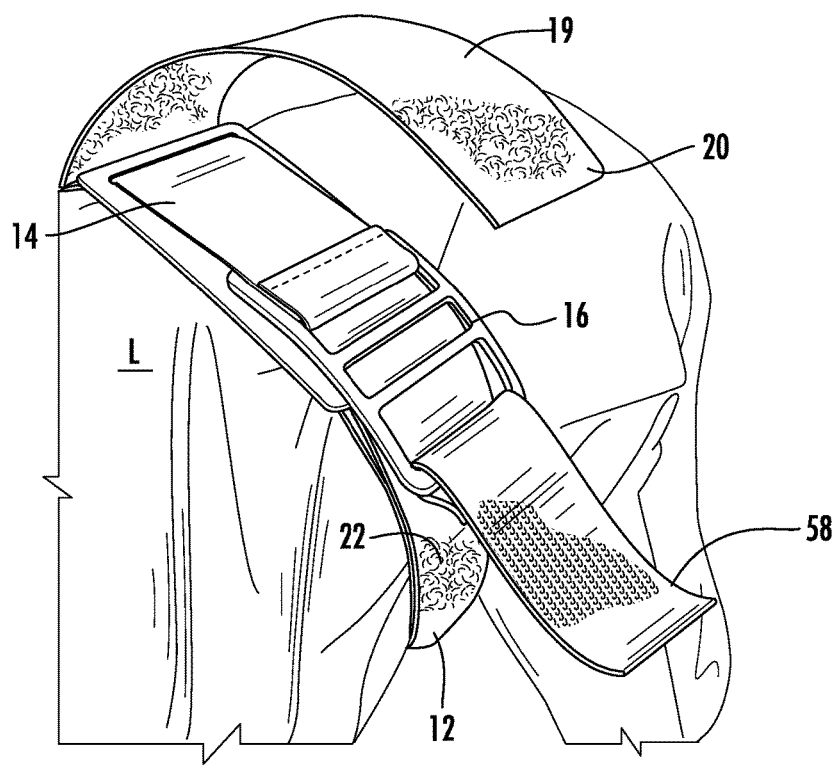
FIG. 16 is a perspective view showing a fourth step in using the tourniquet of FIG. 1, with the lever moved to a fully tightened position.

If the optional counter-pull handle 76 is used, the user may pull this opposite to the pivoting movement of the lever 16, either to make this step easier or to prevent unwanted movement of the tourniquet 10 relative to the limb L. FIG. 16 shows the lever 16 in the fully tightened position.

Figure 17:
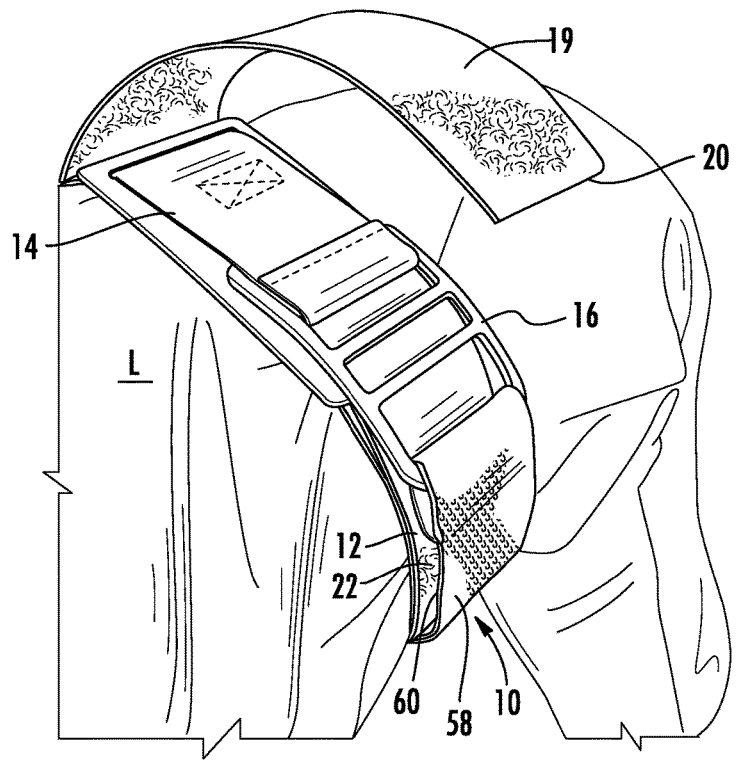
FIG. 17 is a perspective view showing a fifth step in using the tourniquet of FIG. 1, with the lever being secured in the fully tightened position.

Once the lever 16 has been pivotally actuated, it may be secured in the tightened position. For example, FIG. 17 shows the lock tab 58 connected to the strap 12 using the releasable fastener 60, engaging releasable fasteners 22 of the strap 12. This prevents the lever 16 from moving out of the tightened position. It is noted that the lever 16 has an over-center motion, and so only a small amount of force is required to hold it in the tightened position, even though the tourniquet 10 may be applying a very high clamping force.

Figure 18:
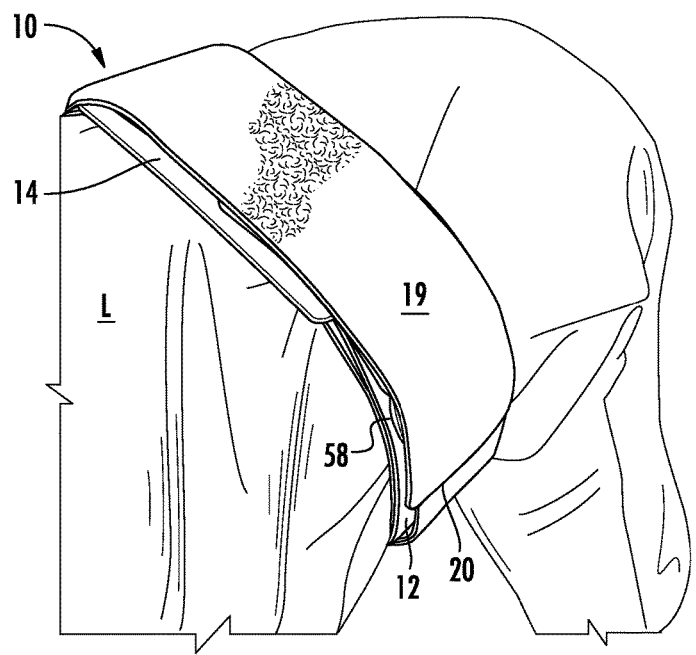
FIG. 18 is a perspective view showing a sixth step in using the tourniquet of FIG. 1, with the excess strap being secured over the lever.

Once the tourniquet 10 has been applied and the lever 16 secured by the lock tab 58, the free end of the strap 12 may be wrapped around the body of the tourniquet 10, covering the baseplate 14, lever 16, and lock tab 58, and secured to the lock tab 58, as shown in FIG. 18. Thus secured, it performs a function of cutting off blood flow, with a very small exterior profile and no protruding exterior element that could protrude, catch on objects, or become dislodged from its locked position, limiting the user's mobility and possibly causing additional injury.

Figure 19:
FIG. 19 is a schematic side elevational view showing an alternative, concave-curved baseplate in a first condition.
Figure 20:
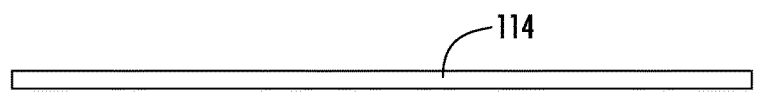
FIG. 20 is a schematic side elevational view showing the baseplate of FIG. 19 in a second condition.
Figure 21:
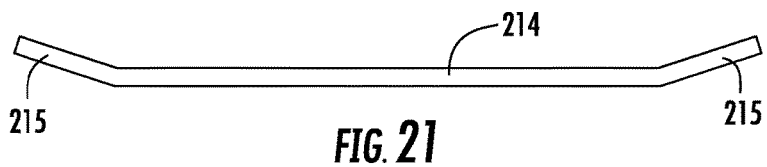
FIG. 21 is a schematic side elevational view showing an alternative, ramped baseplate.

The baseplate 14 may not be completely rigid and therefore will tend to bend in a convex shape, conforming to the curvature of the limb L, when the tourniquet 10 is applied. It is possible under some circumstances that the corners or edges of the baseplate 14 might tend to cause pinching of the limb L. This possibility may be addressed with the use of a baseplate which is concave-curved in a resting state. FIG. 19 shows a baseplate 114 with this concave curvature. This may be substituted for the baseplate 14 described above. Thus curved, the baseplate would be spaced away from the limb L and would not tend to pinch. When the tourniquet 10 is applied and tightened, the baseplate 114 would tend to flatten out to a deflected shape is shown in FIG. 20. As another option to address potential pinching, the center of baseplate may be flat, and the distal ends of the baseplate may be bent at an angle, curved, or otherwise displaced, in a direction towards the lever 16. These ends have a similar effect in preventing pinching to the curvature described above. This feature may be referred to as the distal ends being "ramped". FIG. 21 shows a baseplate 214 with ramped ends 215.

Several of the features of the tourniquet 10 described above can be integrated into the baseplate in order to simplify its construction. For example, FIG. 23 illustrates a tourniquet 310 constructed using an alternative baseplate 314 along with a strap 12 and lever 16 as described above.

The baseplate 314 is a relatively thin, plate-like rigid or semirigid member. Nonlimiting examples of suitable material for the baseplate 314 include plastics, wood, metals, and combinations thereof. In the illustrated example, the baseplate 14 is constructed as an injection-molded polymeric component with a generally rectangular plan view shape. It has first and second ends 332, 336, respectively, and these ends may be ramped as described above.

The baseplate 314 includes a strap guide 330 in the form of a slot formed near the first end 332 of the baseplate 314. The first portion 17 of the strap 12 is threaded through the strap guide 330.

The baseplate 314 includes an integral lever anchor 334 between the first and second ends 332, 336. In the illustrated example, the lever anchor 334 comprises a resilient flange 338 formed integrally with the body of the baseplate 314.

As used herein, the term "integral" refers to components which functionally and/or physically form part of a unitary or monolithic whole. For example, components which are machined from a single piece of material, formed as part of an additive manufacturing process, or formed as part of an injection molding process may be considered physically and functionally integral, unitary, or monolithic. As another example, separate components which are securely attached to each other by means such as fasteners, mechanical joints, thermal or sonic bonding, or adhesives, may be considered functionally integral, unitary, or monolithic.

The flange 338 is shaped so as to define a transverse channel 339 which captures the first pivot element 48 of the lever 16. The flange 338 may be constructed so as to lie tightly against the surface of the baseplate 314, and may include an upturned lead-in feature 340 at its distal end. This facilitates initial assembly, by permitting the lever 16 to be forced between the flange 338 and the baseplate 314. Once the lever enters the channel 339, the flange 338 snaps back into place against the surface of the baseplate 314, and strongly resists removal of the lever 16.

In the illustrated example, a resilient hook 362 is integrally formed as part of the baseplate 314, positioned at or near the second end 336. The hook 362 may be constructed so as to lie lightly against the surface of the baseplate 314, and may include an upturned lead-in feature 364 at its distal end.

A ring 365 with a generally rectangular shape and made of a rigid material such as metal or plastic is attached to the second portion 19 of the strap 12. The ring 365 includes a first slot 367 which is sized to fit the strap 12 with a relatively "tight" (e.g., friction) fit. The exposed portion of the ring 365, and a second slot 369, are collectively sized to fit the hook 362. In the illustrated example, the strap 12 is simply passed through the first slot 367. In use, the end of the ring 365 can be engaged with the lead-in feature 364 and then pulled into full engagement with the hook 362. The spring tension inherent in the hook 362 is made sufficiently light that the ring 365 can be easily removed if necessary.

Once the ring 365 is engaged in the hook 362, the second portion 19 of the strap 12 can be pulled to a desired position (i.e., adjusted), and then folded back and connected to the remainder of the strap 12 using the releasable connector 22. The combined structure of the hook 362 and the ring 365 is another example of a "connector assembly".

The baseplate 314 may optionally incorporate a latch or other similar mechanism (not shown) similar to the latch 59 described above.

The baseplate 314 may incorporate a slot 337 at or near the second end 336. This is similar to the slots 40 described above, and may be used as an alternative to the hook 362 to connect the second portion 19 of the strap 12, in the manner described above.

This version of the baseplate 314 provides for simplified construction and lower parts count. The basic usage of the tourniquet 310 is substantially similar to that of the tourniquet 10 described above.

The tourniquet described above has numerous advantages over pre-existing tourniquets. For example, the tourniquet is of a lighter weight, is a more compact package for easier storage, is easily and more rapidly applied by a user, and has no protruding portions which could limit the users range of motion, become caught on objects and or become dislodged from its locked position rendering the device useless.

The foregoing has described a tourniquet. All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

What is claimed is:

1. A tourniquet, comprising:
    a plate-like baseplate with first and second ends, the baseplate having a strap guide disposed at the first end;
    a strap having first and second ends, the strap having a first portion adjacent its first end, and a second portion adjacent its second end, wherein the first portion is engaged with the strap guide;
    a lever with proximate and distal ends, wherein the proximate end is pivotally connected to the baseplate, and the distal end is free;
    wherein the first end of the strap is pivotally connected to the lever intermediate to the proximal and distal ends;
    a connector assembly operable to selectively connect the second portion of the strap to the baseplate, so as to form a closed loop, the connector assembly operable to permit a length of the closed loop to be adjusted; and
    wherein the first and second ends of the baseplate are both ramped towards the lever, in a configuration which would create a space between a limb and the first and second ends of the baseplate, when the baseplate is placed against the limb prior to tightening of the tourniquet.

2. The tourniquet of claim 1 wherein the strap guide comprises a slot formed in the first end of the baseplate through which the first portion of the strap is threaded.

3. The tourniquet of claim 1 wherein the lever is movable between released and tightened positions, wherein a free length of the strap extending beyond the baseplate is shorter in the tightened position than in the released position.

4. The tourniquet of claim 1 wherein the second portion of the strap includes a releasable connector operable to selectively connect the second portion of the strap to the remainder of the strap.

5. The tourniquet of claim 1 wherein the connector assembly includes:
    a slot formed in the baseplate sized to receive the strap; and
    a releasable connector disposed on the strap and operable to selectively connect the second portion of the strap to the remainder of the strap.

6. The tourniquet of claim 1 further comprising a locking mechanism operable to secure the lever in the tightened position.

7. The tourniquet of claim 1 further comprising a latch carried on the baseplate operable to engage the lever in the tightened position.

8. The tourniquet of claim 1 further comprising a lock tab carried at the distal end of the lever.

9. The tourniquet of claim 8 wherein the lock tab includes a releasable connector operable to selectively connect the lock tab to the strap.

10. The tourniquet of claim 1 wherein the baseplate includes a lever anchor comprising a closed loop of flexible material which surrounds a pivot element of the lever.

11. The tourniquet of claim 1 wherein the baseplate includes a lever anchor comprising a rigid U-shaped element which surrounds a pivot element of the lever.

12. The tourniquet of claim 1 wherein the lever comprises a pair of spaced-apart side rails interconnected by a plurality of crossbars.

13. The tourniquet of claim 1 wherein the baseplate has a concave curvature.

14. The tourniquet of claim 1 wherein a finger hole is formed in the second end of the strap.

15. The tourniquet of claim 1 wherein the strap comprises a plurality of spaced-apart flat sections configured to facilitate cutting.

16. The tourniquet of claim 1 wherein the strap comprises a plurality of spaced-apart cut markings.

17. The tourniquet of claim 1 wherein a counter-pull handle is disposed at the first end of the baseplate.

18. The tourniquet of claim 1 wherein:
the baseplate includes an integral lever anchor disposed between the first and second ends of the baseplate, the lever anchor receiving the proximate end of the lever; and an integral resilient hook positioned at or near the second end of the baseplate; and
a ring sized to fit the hook is attached to the second portion of the strap.

19. The tourniquet of claim 18 wherein the lever anchor comprises a resilient flange shaped so as to define a transverse channel which captures a first pivot element of the lever.

20. A tourniquet, comprising:
a plate-like baseplate with first and second ends, and a strap guide disposed at the first end;
a strap having first and second ends, the strap having a first portion adjacent its first end, and a second portion adjacent its second end, wherein the first portion of the strap is engaged with the strap guide;
a lever with proximate and distal ends, wherein the proximate end is pivotally connected to the baseplate, and the distal end is free;
wherein the first end of the strap is pivotally connected to the lever intermediate to the proximal and distal ends, such that the lever is movable between released and tightened positions, wherein a free length of the strap extending beyond the baseplate is shorter in the tightened position than in the released position;
a locking mechanism operable to secure the lever in the tightened position;
a connector assembly operable to selectively connect the second portion of the strap to the baseplate, so as to form a closed loop, the connector assembly operable to permit a length of the closed loop to be adjusted; and
wherein the first and second ends of the baseplate are both ramped towards the lever, in a configuration which would create a space between a limb and the first and second ends of the baseplate, when the baseplate is placed against the limb prior to tightening of the tourniquet.

21. The tourniquet of claim 20 wherein the second portion of the strap includes a releasable connector operable to selectively connect the second portion of the strap to the remainder of the strap.

22. The tourniquet of claim 20 wherein the connector assembly includes:
a slot formed in the baseplate sized to receive the strap; and
a releasable connector disposed on the strap and operable to selectively connect the second portion of the strap to the remainder of the strap.

23. The tourniquet of claim 20 further comprising a lock tab carried at the distal end of the lever, the lock tab including a releasable connector operable to selectively connect the lock tab to the strap.

24. The tourniquet of claim 20 wherein the baseplate includes a lever anchor which surrounds a pivot element of the lever.

25. The tourniquet of claim 20 wherein the baseplate has a concave curvature.

26. The tourniquet of claim 20 wherein:
the baseplate includes an integral lever anchor disposed between the first and second ends of the baseplate, the lever anchor receiving the proximate end of the lever; and an integral resilient hook positioned at or near the second end of the baseplate; and
a ring sized to fit the hook is attached to the second portion of the strap.

27. The tourniquet of claim 26 wherein the lever anchor comprises a resilient flange shaped so as to define a transverse channel which captures a first pivot element of the lever.

* * * * *